United States Patent [19]

Fauve

[11] 4,310,513

[45] Jan. 12, 1982

[54] METHOD OF PROCESSING AN ACTIVE PRINCIPLE OF A HYDROPHOBIC MEDICAMENT AND PRODUCT THEREOF

[75] Inventor: Robert M. Fauve, Sevres, France

[73] Assignee: Institut Pasteur, Paris, France

[21] Appl. No.: 156,914

[22] Filed: Jun. 6, 1980

Related U.S. Application Data

[63] Continuation of Ser. No. 804,506, Jun. 8, 1977, abandoned, which is a continuation of Ser. No. 539,533, Jan. 8, 1975, abandoned.

[30] Foreign Application Priority Data

Jan. 10, 1974 [FR] France .............................. 74 00842

[51] Int. Cl.³ ..................... A61K 31/79; A61K 47/00; A61K 39/02
[52] U.S. Cl. ....................................... 424/80; 424/88; 424/92; 424/361
[58] Field of Search ..................... 424/80, 88, 92, 361

[56] References Cited

U.S. PATENT DOCUMENTS

| | | | |
|---|---|---|---|
| 2,861,920 | 11/1958 | Dale et al. | 424/80 |
| 2,897,120 | 7/1959 | Cronin et al. | 424/80 X |
| 2,908,614 | 10/1959 | Muggleton et al. | 424/89 X |
| 3,062,712 | 11/1962 | Dale et al. | 424/80 |
| 3,541,201 | 11/1970 | Brown | 424/89 X |
| 4,076,801 | 2/1978 | Fauve | 424/92 |
| 4,180,563 | 12/1979 | Fauve | 424/92 |

FOREIGN PATENT DOCUMENTS

| | | |
|---|---|---|
| 2017373 | 4/1971 | Fed. Rep. of Germany . |
| 2164510 | 2/1975 | France . |
| 1310824 | 3/1973 | United Kingdom . |

*Primary Examiner*—Shep K. Rose
*Attorney, Agent, or Firm*—Weiser, Stapler & Spivak

[57] ABSTRACT

A suspension of the medicament brought to sufficiently fine particle size to be usable subsequently if necessary in injectable suspensions, is produced in the midst of a liquid in which it is itself insoluble and containing in the dissolved state one or several normally solid non-antigenic organic constituents. The solvent is then removed.

17 Claims, No Drawings

METHOD OF PROCESSING AN ACTIVE PRINCIPLE OF A HYDROPHOBIC MEDICAMENT AND PRODUCT THEREOF

This is a continuation of application Ser. No. 804,506, filed June 8, 1977, which is a continuation of Ser. No. 539,533 filed Jan. 8, 1975 both now abandoned.

The present invention relates to a method of processing an active principle of a hydrophobic medicament and to the product thereof.

More particularly the invention relates to the processing of active principles of hydrophobic medicaments or medicaments insoluble in aqueous physiological solutions, in order to prepare injectable suspensions. These active principles of medicaments will be denoted simply, in the following, for convenience of language, by the expression "medicaments". It will also be recalled that the expression "physiological solution" is here taken in its current meaning in pharmacy, that is to say it denotes an isotonic solution containing substances or constituents normally solid in the dissolved state in a physiologically acceptable solvent, mostly water.

It is known that the administration by the parenteral route of a hydrophobic medicament in a physiological solution poses particularly difficult problems. Such is the case, for example, with oestrogens, steroids or hormones, already used as medicaments, or again with the immunostimulant agent described in French patent application No. 71 46520 of the Pasteur Institute. One way of proceeding consists in the administration of suspensions of the medicament in the finely divided state so that all the particles of this medicament have dimensions less than 20 microns, preferably less even than 5 microns, and advantageously than 0.5 micron.

The preservation of such fine suspensions up to the moment of administration or the extempore production of such suspensions are extremely difficult. The suspensions tend to precipitate, the particles of the medicament then agglomerating irreversibly within them. Similar phenomena are observed in the course of attempts to resuspend dry powders of extremely fine particle size in an injectable solution, the particles then remaining stuck together or adhering strongly to the container.

It is an object of the invention to overcome these various drawbacks.

It is a particular object to provide a method of processing such hydrophobic medicaments.

It is another object to provide powders containing these hydrophobic medicaments which are suitable, among other things, for the immediate extempore and easy preparation of directly injectable suspensions thereof.

Other objects, features and advantages of the invention will become apparent from the description which follows.

The method according to the invention is characterised in that a suspension of the medicament brought to a sufficiently fine particle size to be usable subsequently is necessary in injectable suspensions, is produced in the midst of a solvent in which it is itself insoluble and containing in the dissolved state one or several normally solid non-antigenic organic constituents, in then removing the solvent, advantageously but not necessarily by lyophilisation. Preferably the solvent concerned is water, notably apyrogenic distilled water.

Preferably, the amount of non-antigenic organic constituent utilized is sufficient with respect to the content of medicament of the initial solution for the particles to be individually practically embedded or coated in the dry mass of the constituent after the removal of the solvent. In particular, when the drying had been carried out by lyophilisation, a porous solid is obtained whose principal constituent is constituted by the non-antigenic constituent, which plays the role of embedding matrix with respect to the individual particles of the medicament which are embedded in its mass.

The invention relates also to the dry mass as obtained by the above-mentioned method, which mass is characterised by fine particles, less than 20 microns, preferably than 5 microns, and preferably again less than 0.5 microns, of a hydrophobic medicament coated or embedded in a physiologically acceptable non-antigenic constituent. In a preferred form of the invention, the dry mass is in the form of a porous solid in which the particles of the hydrophobic medicament are coated. In this form, the medicament is easy to handle, to transport and to preserve.

The placing in contact of a given weight of this dry mass with the weight of a physiologically acceptable solution, notably aqueous, in which the solid constituent is soluble, which permits the formation of an isotonic solution, leads to the rapid and extempore obtaining of a directly injectable suspension of the medicament in an isotonic solution. In fact, the solubilisation of the constituent results in the resuspension of the individual particles of the medicament, without risk of agglomeration.

In the case where the non-antigenic constituent is constituted by a substance of which the solutions of variable concentrations can be injected into a patient without serious drawbacks, recourse can be had to a physiological serum, for example an isotonic chloride solution to form said directly injectable suspension. There are to be mentioned, by way of example of such non-antigenic substances, certain varieties of dextrans.

In the preferred embodiments of the invention, recourse will however be had to non-antigenic constituents, which are in fact themselves constituted, at least in part, by one or several organic constituents adapted to form themselves isotonic solutions. It is thus possible to produce in extempore manner a suspension of the medicament in a directly injectable isotonic solution, by simple bringing into contact of a given weight of the dry mass of non-antigenic constituents containing the medicament with the necessary amount of distilled water for the reconstitution of the corresponding isotonic solution.

Of course, the non-organic constituent of the type concerned may be constituted in part from an organic constituent of an isotonic solution and/or in part from non-antigenic organic constituents whose concentration in the isotonic solutions may be variable, and, if necessary, in part also of a mineral constituent of the type which are also adapted to form isotonic solutions, for example sodium chloride. The placing in suspension of the hydrophobic medicament may then be effected either with distilled water, or with an injectable physiological serum, or with a proportioned mixture of distilled water-physiological serum.

Advantageously there are contacted, in the midst of the initial suspension, at least 5, preferably from 20 to 40, parts by weight of the constituent of the physiological solution per one part by weight of the hydrophobic medicament.

Preferably, recourse is had, in the method and in the product according to the invention, to those non-antigenic constituents whose concentrations in the corresponding isotonic physiological solutions are high. The concentration in medicament of the injectable suspension formed in a given volume of solvent will be, for equal weight of non-antigenic constituent with respect to the medicament itself all the greater as the concentration in non-antigenic constituent required for the constitution of isotonic solutions is higher. These considerations will obviously play a particularly important role in the choice of the coating constituent for the particles of the medicament, especially when it would appear necessary to administer relatively high doses of medicaments to patients.

In this respect, those of the non-antigenic constituents are advantageously used which are capable of forming aqueous physiological solutions in which they occur at high concentrations. By way of example glucose and lactose are mentioned which provide isotonic solutions which contain respectively 50 g/l of glucose and 100 g/l of lactose.

As non-antigenic constituents useful in the invention, it is also possible to mention for example the substances or group of substances taken in the proportions which permit the production of physiological solutions having respectively the following compositions:

(a) dextran: 60 g/l sodium chloride: 9 g/l
(b) dextran: 60 g/l glucose: 50 g/l
(c) polyvinylpyrrolidone: 35.00 g/l sodium chloride: 8.00 g/l potassium chloride: 0.42 g/l calcium chloride ($6H_2O$): 0.50 g/l magnesium chloride ($6H_2O$): 0.05 g/l sodium bicarbonate: 1.68 g/l Normal HCl: 17.1 ml/1l
(d) Same composition as under (c), in which the sodium chloride is replaced by glucose in the proportion of 38 g/l.

The method according to the invention is applied for example to the processing of hydrophobic immunostimulant agents, extracted from animal or bacterial cells, which have been the subject of French patent application No. 71 46520, filed Dec. 24, 1971 in the name of the PASTEUR INSTITUTE. There will be described below two examples of the application of the method according to the invention, applied to the formation of a dry mass containing such a hydrophobic immunostimulant agent and permitting the subsequent extempore formation of a directly injectable fine suspension of this agent.

EXAMPLE 1

Starting with a chloroform solutioan of the immunostimulant agent, there is added thereto an equivalent volume of apyrogenic distilled water containing 50 g/l of glucose. An inert gas is then bubbled into the mixture, for example nitrogen or a 90% air and 5% carbon dioxide mixture, this bubbling being continued until the complete removal of the chloroform. The immunostimulant agent initially contained in the chloroform solution hence passes into suspension in the aqueous phase in the course of this bubbling operation.

Homogenisation of the suspension then follows by resorting to current milling techniques in the liquid phase, until the dimensions of all the particles of the active agent have become less than 5 microns. Lyophilisation of this suspension then follows to obtain a porous mass containing the extremely fine individual particles of the immunostimulant agent coated in the true matrix constituted by the glucose.

The restoring in contact of the dry mass with water taken in a volume corresponding to 1 liter per 50 grams of glucose contained in the dry mass permits the direct reconstitution of a suspension of the medicament in the divided state in the midst of a physiological solution which can if necessary be injected directly into patients.

EXAMPLE 2

The immunostimulant agent from the initial chloroform solution is made to pass into an aqueous solution under the same conditions as in Example 1, the amount of water employed being such that a suspension is obtained containing 5 mg/ml of immunostimulant agent. Homogenisation of the suspension then follows until the dimensions of all the particles of the immunostimulant agent have become less than 5 microns. There is also prepared a solution of dextran and of glucose in apyrogenic distilled water so as to obtain a solution containing 120 g of dextran and 100 g of glucose per liter. With stirring and very slowly 1 volume of this dextran and glucose solution is added to 1 volume of the suspension.

The mixture obtained is divided up in lyophilisation bottles in the amount of 2 ml of mixture per bottle, and lyophilisation is proceeded with.

The bottles sealed under nitrogen may be stored and transported. An injectable dose is prepared in extempore manner by simply taking up the lyophilisate in 2 ml of apyrogenic distilled water.

EXAMPLE 3

A solid mass containing the abovesaid immunostimulant agent is prepared, by proceeding as in Example 2, but by resorting to a solution of lactose in apyrogenic distilled water containing 193.4 gr per liter of lactose. As in Example 2, one volume of this solution of lactose is stirred very slowly with one volume of the abovesaid suspension and lyophilisation of the mixture is then proceeded with, after its division into lyophilisation bottles, in the amount of 2 ml of mixture per bottle.

As in the preceding case, an injectable dose is prepared in extempore manner, by simple taking up of the lyophilisate in 2 ml of apyrogenic distilled water.

As is self-evident, and as emerges already from the foregoing, the invention is in no way limited to those types of application, nor to those embodiments of its various parts, which have been more especially envisaged; it encompasses, on the contrary, all modifications.

I claim:
1. A dry solid containing particles of a hydrophobic medicament dispersed within a matrix wherein the medicament
   is insoluble in an aqueous physiological solution
   is capable of being in the form of particles having a size greater than that suitable for injection
   is reducible to particle size, less than 20 microns for use as an injectable powder by milling or homogenization
   said fine particles being prone to irreversible agglomeration
said matrix is formed of a water-soluble organic non-antigenic constituent
said non-antigenic constituent and said medicament are in a weight ratio of at least 5 and
said medicament particles are individualized and embedded within said matrix to such an extent as to be releasable within an aqueous medium by solubiliza- tion of said non-antigenic constituent in an aqueous medium when said solid is contacted with an aqueous solution to form an injectable suspension of individualized particles of said medicament.

2. The dry solid of claim 1 which is porous.

3. The dry solid of claim 1 which is a powder.

4. The dry solid of claim 1 wherein the weight ratio of non-antigenic constituent to medicament is from about 5 to about 40.

5. The dry solid of claim 4 wherein the weight ratio of non-antigenic constituent to medicament is from about 20 to about 40.

6. The dry solid of claim 4 wherein the non-antigenic constituent is capable of forming an aqueous physiological solution of high concentration.

7. The dry solid of claim 4 wherein the matrix contains at least one constituent of an aqueous physiological solution.

8. The dry solid of claim 7 wherein the matrix further contains a physiologically acceptable soluble mineral salt, in addition to the solid organic non-antigenic constituent.

9. The dry solid of claim 7 wherein the non-antigenic constituent is selected from among those which are capable of forming an aqueous physiological solution at a concentration from 50 to 100 grams per liter.

10. The dry solid of claim 1 wherein the non-antigenic constituent is selected from the group consisting of polyvinylpyrrolidinone, dextrane, lactose or glucose.

11. The dry solid of any of claims, 1, 2, 3, 4, 5, 6, 7, 8, 9 and 10, wherein the fine particles of said medicament are of a size less than about 5 microns.

12. The dry solid of claim 9 wherein the fine medicament particles are of a size less than 0.5 micron.

13. In a process for making a dry solid containing a non-viable hydrophobic medicament in the form of particles having injectable sizes less than 20 microns and capable to release said particles within an aqueous physiologically acceptable medium when said solid is contacted within an aqueous solution to extemporaneously form a suspension of individualized particles of said medicament suitable for direct injection and wherein said medicament is insoluble in an aqueous physiological solution is capable of being in the form of particles having a size greater than that suitable for injection is reducible to particles sufficiently fine for use as an injectable powder by milling or homogenization said fine particles being prone to irreversible agglomeration forming a suspension of particles of the hydrophobic injectable medicament having a size less than 20 microns in a solution of a solid, organic, water-soluble, non-antigenic constituent, in which said medicament is insoluble, said non-antigenic constituent being in a weight ratio of at least 5 relative to the medicament particles;

lyophilizing the solution obtained and collecting a solid composition of the particles, the particles being embedded in a dry matrix of the said solid, organic, non-antigenic constituent, which solid is adapted when contacted with an injectable physiologically acceptable solution to extemporaneously form said suspension of fine injectable particles of the medicament without agglomeration, and which is suited for direct injection, as a result of the dissolution of said non-antigenic constituent within said injectable physiologically acceptable solution.

14. The process of claim 13 wherein the weight ratio of non-antigenic constituent to medicament is from about 20 to about 40.

15. The process of claim 13 wherein the medicament is in the form of particles having sizes less than about 5 microns.

16. The process of claim 13 wherein the non-antigenic constituent is glucose, lactose, dextran or polyvinylpyrrolidone.

17. The process of claim 13 in which the suspension to be subsequently lyophilized is formed by mixing an organic solution of the hydrophobic injectable medicament with an aqueous solution of the solid organic, non-antigenic constituent, removing the organic phase of the organic solution, thus leaving the hydrophobic injectable medicament particles in suspension in the aqueous solution containing said non-antigenic constituent dissolved therein, milling or homogenizing said particles to said injectable sizes.

* * * * *